United States Patent [19]
van der Walt

[11] Patent Number: 4,827,215
[45] Date of Patent: May 2, 1989

[54] METHOD OF AND APPARATUS FOR MAGNETIC SATURATION TESTING A WIRE ROPE FOR DEFECTS

[75] Inventor: Nicolaas T. van der Walt, Johannesburg, South Africa

[73] Assignee: Crucible, Societe Anonyme, Luxembourg, Luxembourg

[21] Appl. No.: 28,184

[22] Filed: Mar. 19, 1987

[30] Foreign Application Priority Data

Mar. 25, 1986 [ZA] South Africa ................. 86/2214

[51] Int. Cl.⁴ .................... G01N 27/83; G01N 27/90
[52] U.S. Cl. .................................. 324/227; 324/232; 324/242
[58] Field of Search ............ 324/206, 213, 219–221, 324/227, 232–235, 238–243, 214–216; 335/284, 306

[56] References Cited

U.S. PATENT DOCUMENTS

| | | | |
|---|---|---|---|
| 1,992,100 | 2/1935 | Stein | 324/239 |
| 2,065,119 | 12/1936 | Davis | 324/240 X |
| 2,124,579 | 7/1938 | Knerr et al. | 324/220 X |
| 2,889,513 | 6/1959 | Callan et al. | |
| 2,895,103 | 7/1959 | Vogt et al. | 324/239 X |
| 3,242,425 | 3/1966 | Harmon | |
| 3,273,055 | 9/1966 | Quittner | |
| 3,424,976 | 1/1969 | Jezewski et al. | |
| 3,694,740 | 9/1972 | Bergstrand | 324/235 X |
| 3,881,151 | 4/1975 | Bigelow | |
| 3,887,865 | 6/1975 | Brooks | |
| 4,002,967 | 1/1977 | Fennell | |
| 4,399,422 | 8/1983 | Nelson et al. | 355/284 |
| 4,427,940 | 1/1984 | Hirama et al. | 324/240 |
| 4,439,731 | 3/1984 | Harrison | 324/239 |

FOREIGN PATENT DOCUMENTS

| | | | |
|---|---|---|---|
| 0121084 | 10/1984 | European Pat. Off. | |
| 2406136 | 9/1974 | Fed. Rep. of Germany | |
| 2239173 | 2/1975 | France | |
| 2347683 | 11/1977 | France | |
| 0001533 | 1/1980 | Japan | 324/242 |
| 0044839 | 4/1981 | Japan | 324/240 |
| 0230053 | 11/1985 | Japan | 324/232 |
| 0051779 | 9/1966 | Poland | 324/220 |
| 0936033 | 9/1963 | United Kingdom | 324/232 |
| 1539313 | 1/1979 | United Kingdom | |
| 1542933 | 3/1979 | United Kingdom | |
| 2012966 | 8/1979 | United Kingdom | |
| 2071331 | 9/1981 | United Kingdom | |
| 2100440 | 12/1982 | United Kingdom | |

OTHER PUBLICATIONS

Herbert R. Weischedel, "The Inspection of Wire Ropes", Copr 1985, Material Evaluation, vol. 43, No. 13, pp. 1592–1606.

Primary Examiner—Gerard R. Strecker
Attorney, Agent, or Firm—Chilton, Alix & Van Kirk

[57] ABSTRACT

A wire rope tester which can detect broken wires, area reductions, or wire contact irregularities. The tester includes two permanent magnetic stacks which produce axial adjacent and opposed DC magnetic fields which magnetize the rope. Broken wires are indicated by flux variations when the flux density is at saturation; area reductions are related to flux variations; also at saturation flux density; and wire contact pattern changes produce detachable eddy current flux variations when the flux density gradient is constant.

5 Claims, 5 Drawing Sheets

METHOD OF AND APPARATUS FOR MAGNETIC SATURATION TESTING A WIRE ROPE FOR DEFECTS

BACKGROUND OF THE INVENTION

This invention relates to the electromagnetic testing of wire ropes.

Steel hoist ropes are vital components used in many industrial applications and particularly in deep level mining. The ropes are of prime importance from a safety and production point of view and it is therefore necessary that the ropes are examined regularly to ensure that operational standards are consistently being maintained.

Currently, wire ropes are electromagnetically tested to determine variations in three characteristics, namely the cross-sectional area of the rope, wire contact within the rope, and broken wires. Each of these characteristics is hereinafter briefly commented upon.

Cross-sectional area: the strength of a rope is dependent on its cross-sectional steel area which can, for example, be reduced by normal wear and tear, corrosion, and stretch necking of a weak part.

Wire contact: a rope is made up of strands which in turn are made up of individual carbon steel wires wound together in a particular pattern or lay. Each wire makes physical contact with adjacent wires in a particular fashion, the total effect of which is characteristic of the rope in question. If a rope is damaged, for example by having been kinked or bent beyond its elastic limit, the contact pattern of the wires changes. It is important to detect such changes in contact pattern for they may precede a failure of the rope.

Broken wires: a multiplicity of broken wires over a short length of a rope seriously affects the strength of the rope. Broken wires arise from a variety of causes such as, for example, vibration modes which are set up in the ropes during the cycle of acceleration, steady speed and deceleration. It is clearly important to detect broken wires wherever they may be inside a rope.

Historically the cross-sectional area of a rope and the wire contact characteristic have been measured with a device referred to as an AC rope tester. Such a device is disclosed, for example, in the specification of South African Pat. No. 69/6054. The broken wire characteristic on the other hand has been measured with the aid of an instrument referred to as a DC rope tester typified for example in the specification of South African Pat. No. 69/6269. The applicant is also aware of cross-sectional area measurements having been made with a DC rope tester.

Other literature of which the applicant is aware is the specifications of U.K. Pat. Nos. 1231641, 1476773, 1504404, 1531825, and 1565508 and French Pat. No. 2083900.

To the applicant's knowledge the aforementioned rope characteristics have hitherto been measurable only by employing two distinct instruments.

Modern requirements arising from the demands for increased productivity, simplicity, cost effectiveness, and the availability and expertise of skilled non-destructive testing personnel have demonstrated the need for a single instrument which is capable of simultaneously measuring each of the three aforementioned characteristics.

SUMMARY OF THE INVENTION

The invention provides a method of testing a wire rope which includes the steps of establishing at least two magnetic fields, using the magnetic fields to magnetise adjacent sections of the rope in opposing directions respectively, establishing relative movement between the magnetic field and the rope, and monitoring the resulting magnetic flux in the rope for variations which are due to irregularities in the rope.

Preferably the magnetic fields are DC fields.

Preferably the rope is caused to move through the DC fields.

In one form the method of the invention includes the steps of causing the rope to move along a path, the longitudinal axis of the rope along the path being substantially aligned with the path, establishing a first magnetic field over a first portion of the path, establishing a second magnetic field over a second portion of the path which is adjacent the first portion, the first and second fields being directed in opposing senses along the path whereby the rope is magnetised in opposing axial directions as it moves along the path, and monitoring a resulting magnetic flux in the rope for variations which are due to irregularities in the rope.

In accordance with the invention area variations are detected by monitoring variations in the magnetic flux which are a function of the travel of the rope past a predetermined reference point i.e. variations of flux in the rope which occur as the rope traverses the magnetic fields.

Preferably the flux variations are monitored when the magnetic flux in the rope is at or close to a saturation flux density. In addition the flux value is substantially constant, at saturation.

According to a different aspect of the invention broken wires are detected by monitoring magnetic flux variations in the rope with the flux density in the rope at or close to a saturation flux density.

Variations in flux density arising on the one hand from area variations and on the other hand from broken wires in the rope are distinguishable by processes and techniques which are known per se. As area variations are directly related to flux variations they are easily detected. Broken wires can be detected by means of two probes which are spaced apart a predetermined distance in the axial direction of the rope. Broken wires in the rope produce predictable signals which are detected by the probes, and which are processed in a known way to provide an indication of the broken wires.

In accordance with a different aspect of the invention, changes in the wire contact pattern in the rope are detected by monitoring variations in the total eddy current flux which is induced in the rope during its passage through the opposing magnetic fields. More particularly an eddy current flux which is characteristic of the wire rope with a given contact pattern amongst the wires in the rope is monitored for variations which arise as a result of contact between adjacent wires in the rope being broken or otherwise being disturbed. Thus the eddy current flux measurement is then not affected by magnetic flux-dependent factors.

The flux density at the monitoring point may be nominally zero. Further, the rate of change of flux density, relatively to the rope length, may be constant. The eddy current flux measurement is then not affected by other magnetic flux-dependent factors and, consequently, if the contact pattern changes the eddy current flux hanges and this is detectable.

The invention further extends to apparatus for testing a wire rope which includes means for establishing first and second magnetic fields, the rope being movable through the magnetic fields whereby adjacent sections of the rope are magnetised in opposing directions, and means for monitoring the resulting magnetic flux in the rope for variations which are due to irregularities in the rope.

The magnetic fields which are established are preferably DC fields. The fields are located adjacent one another and are directed in opposite senses. The fields may make use of a common pole piece.

The fields may be in axial alignment.

The magnetic flux in the rope may be monitored by means of any suitable transducers such as Hall effect instruments or similar devices, search coils, or similar mechanisms which are responsive to flux variations. The manner in which the signals, which are generated by these devices, are processed to provide the necessary information is known per se and therefore is not elaborated on in this specification.

The invention also extends to a magnetising head for use in testing a wire rope which includes a first permanent magnet stack which in use establishes a first magnetic field, a second permanent magnet stack which in use establishes a second magnetic field, the first and second fields being adjacent one another and being directed in opposite senses, and a pathway being formed so that the rope can travel through the first and second fields whereby the rope is magnetised by the fields in opposing directions.

The first permanent magnet stack may include a first pole piece and a second pole piece, and the second permanent magnet stack may share the second pole piece and include a third pole piece. The first and third pole pieces are of the same polarity.

Each magnet stack may consist of one or more arrays of permanent magnets which are radially spaced from the pathway along which the rope travels.

The fields which are produced in the apparatus and in the magnetising head may be of equal amplitude or strength although of opposite senses and may have the same length in the direction of rope travel.

At least one field should have a value which induces a magnetic flux which is in saturation for each rope size with which the magnetising head will be used.

In a variation of the invention the fields may vary as to the maximum magnetic strength of each field and as to the distance, in the direction of rope travel, over which the field extends. In this instance the rope is preferably subjected to the influence of the higher magnetic field first and then to the opposing influence of the lower magnetic field.

BRIEF DESCRIPTION OF THE DRAWINGS

The invention is further described by way of examples with reference to the accompanying drawings wherein.

DESCRIPTION OF PREFERRED EMBODIMENTS

The principles of the invention are described hereinafter firstly by examining the theoretical basis of the invention and thereafter by considering the practical implementation of these principles.

THEORETICAL CONSIDERATIONS

As indicated in the preamble to this specification it is an object of the present invention to provide a single device which is capable of simultaneously and independently determining (a) variations in the cross-sectional area of a steel rope, (b) the presence of broken wires in the rope, and (c) irregularities in the contact pattern established by the wires in a rope.

CROSS-SECTIONAL AREA

If a wire rope is magnetised in its axial direction then the magnetic flux $\phi$ established in the rope is given by the expression:

$$\phi = BA \quad (1)$$

which can be rewritten as:

$$\phi = \mu H A \quad (2)$$

Where
B is the magnetic flux density in the rope,
A is the cross-sectional steel area of the rope,
$\mu$ is the magnetic permeability of the steel in the rope, and
H is the magnetising force.

The variation of the magnetic flux in the rope with respect to its axial length, designated 1, is given by the expression:

$$\frac{d\phi}{dl} = \mu H \frac{dA}{dl} + \mu A \frac{dH}{dl} + HA \frac{d\mu}{dl}$$
$$= B \frac{dA}{dl} + \mu A \frac{dH}{dl} + HA \frac{d\mu}{dl}$$

It is necessary to isolate variations in magnetic flux which arise as a result of variations in the cross-sectional steel area of the rope. The relevant term in equation (4) is the first term and, assuming the effects of the second and third terms are zero or negligible, it follows that B must be constant if flux variations are to be related directly to area variations. In other words:

$$\frac{dB}{dl} = 0 \quad (5)$$

Equation (5) may be satisfied by providing magnetising means through which the rope passes and which establishes a flux density pattern in the rope which reaches a maximum value, or a constant value, at least at one point. For example if the flux density B approaches the saturation flux density $B_s$, then $dB/dl \to 0$.

Under these conditions flux variations are given by the expression:

$$\frac{d\phi}{dl} = B_s \frac{dA}{dl} \quad (6)$$

and the saturation flux, $\phi_s$, may be expressed as:

$$\phi_s = AB_s \quad (7)$$

The second and third terms in equation (4) are resolved as follows. (dH/dl) is a parameter of the magnetising means i.e. the test head and if the magnetising force is constant in the test area i.e. independent of rope length then $dH/dl = 0$.

$\mu$ is not constant but is a function of B. However as the magnetising force H increases $\mu$ tends asymptotically to a constant value which is characteristic of the material of the rope. This limiting value is not achieved but the higher H is the more constant is $B_s$ and consequently the more constant is the permeability $\mu$. It follows therefore that the magnetising means should induce the highest possible magnetic flux density in the rope and that ideally at least one point of the rope should be fully saturated magnetically as it passes through the test head and, moreover, the flux density should be as constant as possible over that portion of the length of rope which is required to make a measurement of flux variations with rope length (refer to equation (6)).

BROKEN WIRES

If the rope is magnetised in its axial direction and there is a broken or cracked wire in the rope then the magnetic effect of the broken wire manifests itself as a dipole with a magnetic moment $M_d$ given by the expression:

$$M_d = B \, a \, l \quad (8)$$

Where a is the cross-sectional area of the broken wire or the crack, l is the axial separation of the broken ends or the axial length of the crack, and B is the flux density.

For the magnetic moment $M_d$ to be proportional only to the product "al" i.e. to the volume of the irregularity, $B = \mu H$ must be constant.

Thus, for detecting broken wires, the magnetising means should induce a flux density in the rope, as it passes through the test head, which is as high into saturation flux density $B_s$ as possible, for this causes $\mu$ asymptotically to approach its limiting value, and which is as constant as possible over the length of the rope required to detect the passage of the broken wire dipole at the speed at which the rope passes through the test head.

Under these conditions $$\phi_d = M_{d/l} = B_s \, a \quad (9)$$

WIRE CONTACT IRREGULARITIES

Irregularities in the wire rope arising from variations in the wire contact pattern manifest themselves by causing variations in the flux which is established in the rope by eddy currents. These eddy currents fall into at least two principal categories, namely the eddy currents which are established in the individual wires, referred to as area eddy currents and the eddy currents which circulate from wire to wire i.e. contact eddy currents. These effects are considered on an idealised basis only but it is to be understood that the following analysis is generally applicable to ropes which deviate from the ideal and that in these ropes eddy current flux variations are also detectable.

AREA EDDY CURRENTS

Figure 1:
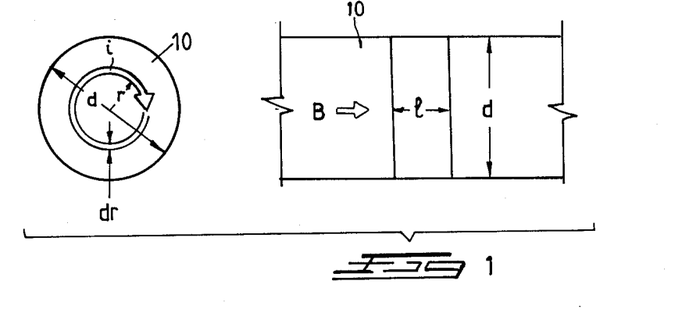
FIG. 1 illustrates a portion of a wire in which eddy currents are induced.

FIG. 1 illustrates a portion 1 of a length of circular steel wire 10 and of diameter d.

If an axial magnetic field B is established in the wire and this field is variable with time then circular eddy currents are induced in the wire, the amplitudes of the currents being continuous functions of their respective radii. These effects are well known. The cross-sectional view of FIG. 1 depicts an incremental annulus of radius r and of thickness dr in which is induced an eddy current i. It can be shown that the total circular eddy current I in the wire is given by the expression:

$$I = \frac{gld^2}{16} \frac{dB}{dt} \quad (10)$$

Where:

g is the electrical conductivity of the steel in mhos per meter, l is the axial length of wire in meters in which the eddy currents flow, d is the diameter of the wire in meters, and $\frac{dB}{dt}$ is the rate of change of the axial flux density in the wire in Teslas per second.

By Ampere's theorem the current flowing in a closed loop is equivalent to a dipole whose magnetic moment is a product of the amplitude of the current, the area of the loop and the permeability of the material within the loop. Using this theorem the equivalent magnetic moment $M_a$ of the total eddy current I is given by the expression:

$$M_a = \frac{\pi}{128} \mu' \, gld^4 \frac{dB}{dt} \quad (11)$$

Where $\mu'$ is the magnetic permeability of the wire at the value of the flux density B where dB/dt takes place.

A wire rope is far more complicated than a single wire and an exact mathematical analysis of such a rope in these terms is not possible. However for a strand which includes n identical round wires, which do not touch one another, the total magnetic flux $\phi_a$ which is established by the eddy currents flowing in the n individual wires, referred to as the "area eddy current magnetic flux" may be derived from equation (11) and is given by the expression:

$$\phi_a = \frac{1}{n\pi 8} \mu' g A^2 v \frac{dB}{dl} 1 \qquad (12)$$

Where v is the rope speed, and
A is the total steel area of the n wires.

The flux $\phi_a$ opposes the main flux which is induced in the rope by the magnetising means. It should also be noted that:

$\phi_a = 0$ if $(dB/dl) = 0$.

CONTACT EDDY CURRENTS

If the n wires in the strand, referred to, touch one another, then the area eddy currents still flow in each wire and the flux $\phi_a$ given by equation (12) is still established.

Figure 2:
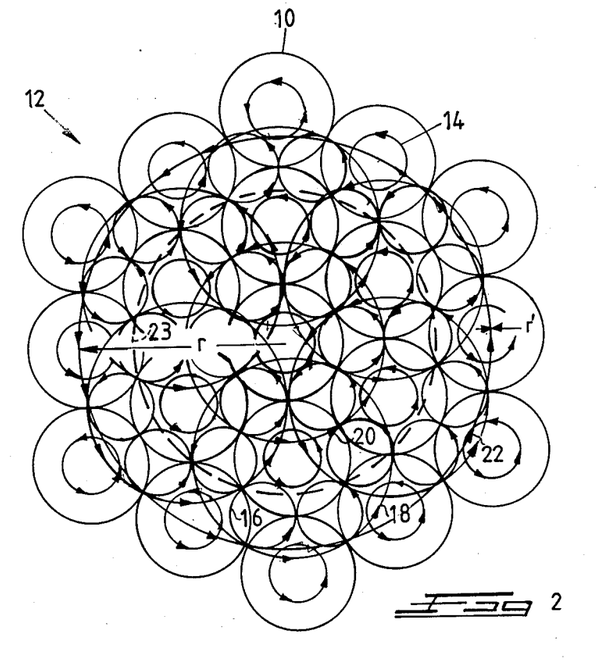
FIG. 2 is a cross-sectional view of a strand of a rope which includes nineteen wires and illustrating eddy currents which are induced in the strand.

FIG. 2 illustrates the situation which prevails when an ideal steel wire strand 12 which includes nineteen wires 10, touching one another, is subjected to a varying magnetic field which establish eddy currents in the strand.

In the first instance eddy currents designated by arrowed circles 14 are established in each of the wires. These are the "area eddy currents" which each give rise to the flux $\phi_a$ of equation (12).

Secondly wherever three adjacent wires touch one another local eddy currents indicated by arrowed circles 16 are induced. In this illustrated example there are twenty four of these contact eddy current paths. The amplitude of each of these eddy currents is dependent on dB/dt, the magnetic area which each circle encloses, the conductance of each circular path, and the three "contact" conductances where the wires touch.

At each contact point two equal eddy currents oppose each other so that the net effect of the local eddy currents 16 is zero.

Eddy current paths designated by larger arrowed circles 18 (six in total) are also established. These circles include considerably more magnetic material than the circles 16 but similar reasoning applies in that the circles 18 have six contact points. However there are also six contact points in the strands where the eddy currents represented by the circles 18 oppose each other so that the net effect of these eddy currents is also zero.

A single circular eddy current path, designated 20, is established where the six wires of the inner layer contact each other with the geometric centre of the strand as the centre of the path. In this case the eddy current is unopposed. In the same way another single circular unopposed eddy current path 22 is established where adjacent wires of the twelve wires in the outer layer touch one another, and a third single circular unopposed eddy current path 23 exists between the paths 20 and 22.

In the idealised example shown in FIG. 2 the net eddy currents are produced by the area eddy currents which are shown by the circles 14, and the contact eddy currents which are represented by the concentric circles 20, 22 and 23. If contact between any two or more wires is broken or changes then:

(a) the magnetic moments due to the area eddy currents (the circles 14) remain unaffected, (b) the magnetic moments of the contact eddy currents (circles 16 and 18), which were zero, remain zero, and, (c) the magnetic moments due to the contact eddy currents (circles 20, 22 and 23) are grossly affected if contact between adjacent wires in the same layer of wires is broken but not necessarily so if contact between adjacent wires in different layers is broken.

The principle which has just been expounded may be applied to an ideal strand which consists of any number of wires.

It can be shown for every eddy current path x of the type represented by the circles 20, 22 and 23 in the ideal case shown in FIG. 2, where all the contact areas between the wires are the same, that the opposing magnetic flux in the rope due to this eddy current path x is:

$$\phi_{cx} = \mu' v \frac{dB}{dl} (A_x)^2 r'_x \left[ \frac{1}{\frac{2\pi r x}{9} + \frac{1}{9xl} + \ldots + \frac{1}{9xm}} \right] \qquad (13)$$

where:

g = conductivity of the steel, from which the rope is made, in mhos/m, $A_x$ is the ferromagnetic area enclosed by the eddy current path x, $r_x$ is the radius of the eddy current path x, $r'_x$ is the radial contact distance where wires touch, m is the number of contact points in the eddy current path x, and $g_{x1}$ to $g_{xm}$ are the individual contact conductivities, in mhos per square meter, of each of the m contact points in the eddy current path x.

It is to be noted that if the n'th contact between any two or more adjacent wires is broken then the respective contact conductivity value $g_{xn}=0$, and $\phi_{cx}=0$ irrespective of any other parameter in equation (13).

Clearly variations in the contact pattern between adjacent wires in a rope are manifested in variations in $\phi_{cx}$. The essential requirement in the rope magnetising means which may be deduced from equation (13) is that there must be a rate of change of magnetic flux density with time at the instant of measurement i.e. the terms v and dB/dl in equation (13) must not be zero.

The total flux $\phi_{ct}$ which arises from the contact eddy current paths, referred to as the contact eddy current flux in the rope, is given by the summation (designated S) of the fluxes for each of the paths x, and may be expressed as:

$$\phi_{ct} = S(\phi_{cx}), \text{ for all x.} \qquad (14)$$

TOTAL EDDY CURRENT FLUX

The total eddy current flux $\phi_e$ in the rope which opposes the main flux is given by the expression:

$$\phi_e = \phi_a + \phi_{ct} \qquad (15)$$

and this, using equations (12), (13) and (14), may be expressed as:

$$\phi_e = \mu' v \frac{dB}{dl} F \qquad (16)$$

-continued $$\text{Where } F = \frac{gA^2}{n8\pi} +$$  (17)

$$S(A_x)^2 r_x \left[ \frac{1}{\frac{2\pi r x}{9} + \frac{1}{9xl} + \cdots + \frac{1}{9xm}} \right], \text{ for all } x$$

From equation (16) it is apparent that if there is no variation of flux density per axial rope length, or if the rope is at a standstill i.e. v=0, no eddy currents are established in the rope and no contact measurements are possible.

The total eddy current flux in the rope $\phi_e$, is proportional to the permeability $\mu'$ at the instant of measurement. $\mu'$ assumes its highest value, for practical terms, at the optimum point on the rope's hysteresis curve for measuring eddy currents. It is known that physical mechanical damage like a hard blow or shock or a bend beyond the elastic limit affects the permeability of steel at those places. Such damage therefore affects $\mu'$ and is reflected in the measurable quantity $\phi_e$.

PRACTICAL REALISATIONS OF THE INVENTION BASED ON THE AFOREMENTIONED THEORETICAL CONSIDERATIONS

In the first instance it is to be noted that the preceding analysis relates to an ideal situation and that at least to some extent reflects a first approximation only to a full understanding of the magnetic effects. A more detailed analysis does not affect the principle of operation. Consequently it is possible to devise a practical instrument for accurate rope testing using the understanding, and the equations, hereinbefore outlined.

As indicated it is an object of the present invention to provide a single device which is capable of separately but independently detecting area variations, broken wires and contact irregularities in a wire rope.

Figures 3, 4, 5:
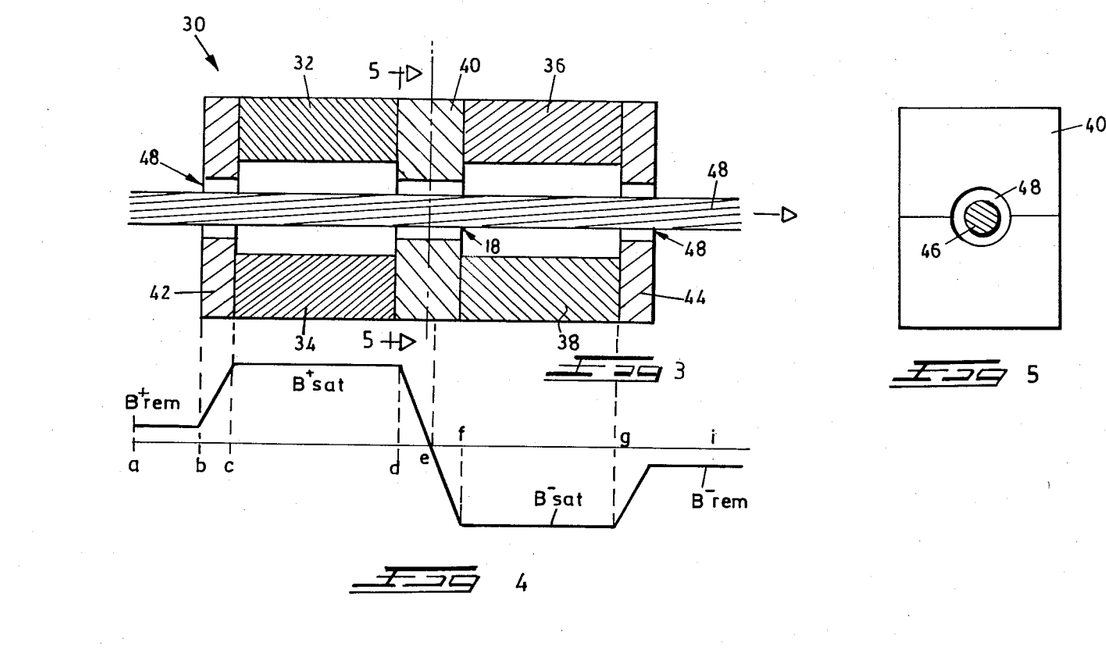
FIG. 3 is a side view in axial cross-section of a magnetic test head according to the invention.
FIG. 4 is an idealised representation of magnetic fields which are induced in a rope passing through the test head of FIG. 3.
FIG. 5 is a cross-sectional view of the head of FIG. 3 on the line 5—5.

FIGS. 3 and 5 illustrate the construction of a composite magnetic test head 30 in axial and radial cross-section respectively. The head includes a first pair of permanent magnet stacks 32 and 34 which are effectively arranged in parallel, and a second pair of permanent magnet stacks 36 and 38 which are also arranged in parallel on appropriate magnetic structure. The magnet stacks share a central north pole 40 and respectively have outer south poles 42 and 44. A wire rope 46 can pass freely through holes 48 which are in line and which are formed in the pole pieces 40, 42 and 44 respectively.

As shown in FIG. 3 the test head magnetises the rope 46, over that portion of its length which is exposed to the magnetic field of the test head, in two opposing directions. FIG. 4 graphically represents an ideal required variation of the magnetic field in the rope 46.

Assume that the rope initially has a remnant flux density $B^+_{rem}$ and that it is moving from the left to the right through the test head of FIG. 3. Referring to the letters a to i marked on FIG. 4, as a reference point on the rope enters the leading south pole at b the flux density rises and at point c reaches the highest saturation flux density which can be achieved with the permanent magnet stack. This is designated $B^+_{sat}$. The saturation flux density is ideally maintained until point d is reached at or near the left boundary of the central pole piece. At this location the effect of the magnetic field in the reverse direction makes itself felt and the flux density decreases, passing through zero, and reaching the maximum value, in the reverse direction, of $B^-_{sat}$, at point f. This reverse saturation flux density is ideally maintained up to point g whereafter the flux density decreases to a remnant value $B^-_{rem}$ which is maintained after the reference point on the rope has left the test head.

At point e the flux density in the rope is zero and in this illustrated ideal case the slope of the flux density versus rope length is given by the expression:

$$\frac{dB}{dl} = \frac{2B_{sat}}{L_p}$$  (18)

Where $L_p$ is the width of the central pole 40, and $B_{sat} = B^+_{sat} = B^-_{sat}$, on the assumption that $B^+_{sat} = B^-_{sat}$.

Thus, in this ideal case, $\phi_s$ (equation (7)) should be measured at an appropriate point between c and d, or between f and g, and $\phi_d$ (equation (9)) should also be measured at a similar location. Between c and d, and f and g, a saturation flux density is maintained at a substantially constant value and $dB/dl = 0$. In other words the total eddy current flux $\phi_e = 0$.

$\phi_e$ on the other hand (equation (16)) should be measured at the point e where the flux density in the rope is zero and hence no effects which are due to area variations or broken wires manifest themselves and equation (16) applies.

It is noted that the point e is not centrally positioned in the pole piece 40 but is offset to the right i.e. in the direction of rope movement. This is due to remnant magnetism in the rope from the leading magnetic field which must be neutralised by a magnetising force, from the lagging magnetic field, equal to the coercivity of the rope.

Figure 6:
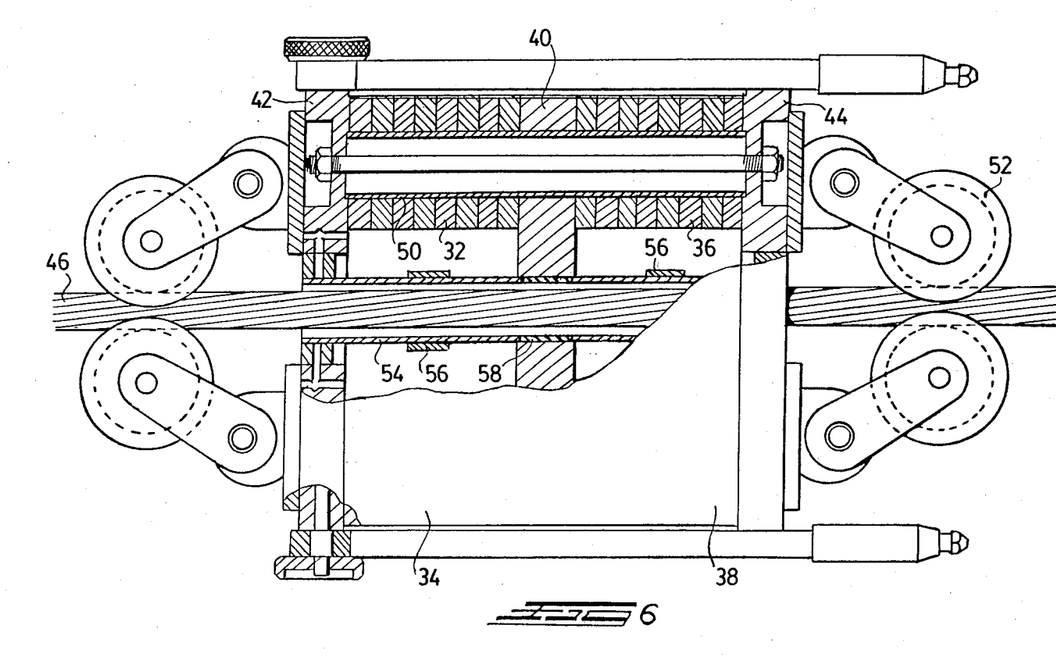
FIG. 6 illustrates from the side a practical composite magnetic test head according to the invention, partly sectioned, FIGS. 7(a) and 7(b) respectively graphically illustrate the variation of the gradient of flux density, and of flux density, with rope length, as a rope is passed through the test head of FIG. 6, which for the sake of convenience is shown schematically adjacent the curves along an abscissa of the same scale.

FIG. 6 illustrates a practical composite test head constructed in accordance with the principles already outlined. Where applicable like reference numerals are employed to indicate similar components to those shown in FIGS. 3 and 5.

Each magnet stack 32 to 38 consists of nine anisotropic strontium ferrite flat magnets each 1.27 cm thick. Each magnet is 9 cm square with a 4.7 cm diameter central hole. The magnets are assembled on a suitable core 50 which passes through the central holes. Each stack is 11.5 cm long i.e. referring to FIG. 3, the spacings between the opposed faces of the pole pieces 42 and 40, and 40 and 44, are respectively 11.5 cm. The south poles 42 and 44 are 2 cm thick and −10 cm wide. The pole area at the air gap is 25 cm². The central north pole 40 is 10 cm wide and 4.4 cm thick.

Guide wheels 52 are located on either side of the test head. These wheels engage the rope 46 which passes through a sheath 54 in the centre of the test head and ensure that the rope is centrally positioned in the test head. Search coils 56 are provided around the sheath. These coils provide a measurement of the flux variations for the purposes already described. If the test head is a permanent installation the coils 56 may be helical. If the test head is a portable device then the coils 56 may be of the saddle type. It is understood that instead of search coils any other appropriate flux measuring device, such as a Hall-effect device, may be used. A suitable magnetic field responsive sensor device 58 is also positioned in the central pole piece for measuring the field about the rope resulting from eddy currents.

Figure 8:
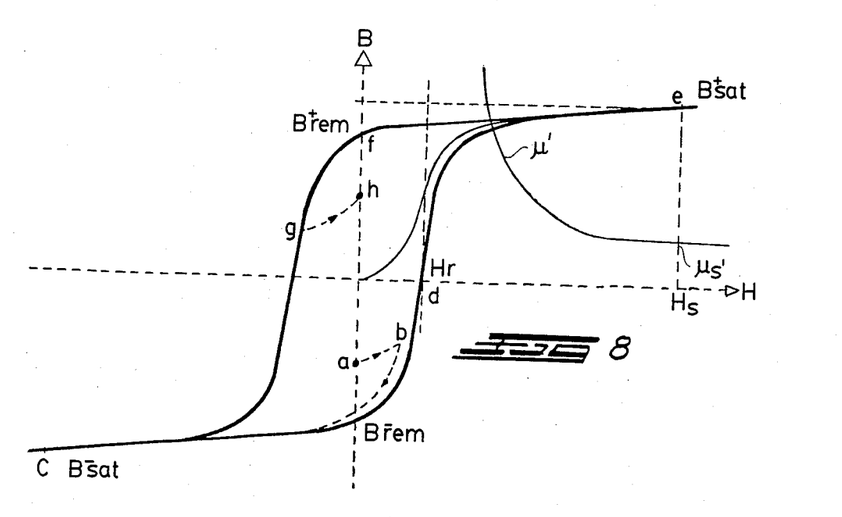
FIG. 8 shows the B-H curve and hysteresis loop of a rope under test in the head of FIG. 3, and FIGS. 9(a) and 9(b), respectively, are curves similar to the curves shown in FIGS. 7(a) and 7(b) obtained with a magnetic test head according to a variation of the invention, which is shown for reference purposes adjacent the curves.

The test rope 46 is a 38 mm diameter multi-layer non-spin rope with a cross-sectional steel area of 716 mm². The electrical conductivity of the rope is 4.7×10⁶ mhos per metre. Its B-H curve, hysteresis loop, and permeability $\mu'$, are shown in FIG. 8.

Figures 7A, 7B:
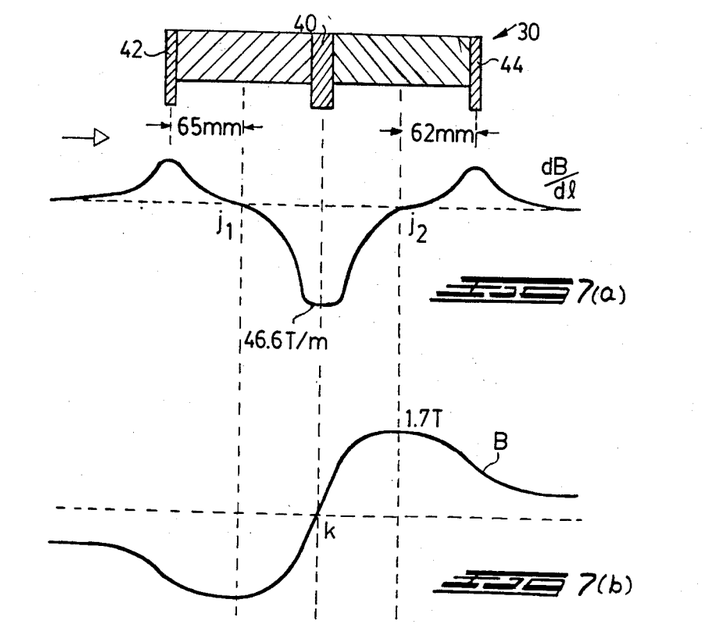

FIGS. 7(a) and 7(b) represent curves of dB/dl, and rope flux density B, respectively, against rope lengths exposed to the magnetic field of the head and referenced to the head 30 itself half of which is shown superimposed.

Using the principles already outlined it is apparent that measurements to detect area variations and broken wires are to be taken either at point $j_1$ or $j_2$ where $dB/dl = 0$. At these points the saturation flux density is approximately 1.7 Tesla.

In the practical test head $j_1$ is 65 mm from the centre of the leading south pole and $j_2$ is 62 mm from the centre of the lagging south pole.

From the hysteresis curve of FIG. 8 the magnetising force $H_s$ which is required to achieve the saturation flux density of 1.7 Tesla in the rope (point e) is 7.5×10³ amps per metre. Tee permeability $\mu'_s$ is 4×10⁻⁵ Tesla meters per amp and is substantially constant.

Contact irregularities which, as has been stated, manifest themselves as circular eddy current anomalies are measured at point k, see FIG. 7(b). At this point the flux density in the rope is zero and $dB/dl = 46.6$ Tesla per meter.

The coercivity Hr on the hysteresis loop for B=0 (point d, FIG. 8) is 1.45×10³ amps per meter. At this point the permeability:

$$\mu' = dB/dH = 3 \times 10^{-3} \text{ Tesla meters per amp.}$$

The point k is, as has been noted, not centrally situated with respect to the central north pole but is offset to the right by a distance which, for a symmetrical composite head, is roughly equal to $H_c/H \times w/2$ where $H_c$ is the coercivity of the rope, H is the test head magnetising force, and w is the width of the central pole. The offset is best found by measurement and for the particular configuration illustrated it was 3 mm. The rope speed was 1 meter/second.

As the rope passes through the test head it follows on its hysteresis loop a path which is marked on FIG. 8 and which extends from point a through the points b, c, d, e, f, g and finally to point h. At this stage the relevant part of the rope is past the lagging south pole. The sections a to b, and g to h, are due to stray magnetic fluxes from outside the leading and lagging south poles respectively.

Irrespective of the magnetic conditions in the rope before or after a test the magnetisation path which extends from point c to point e i.e. between saturation levels in either direction, is always the same, ensuring repeatability of tests.

Figure 9A:
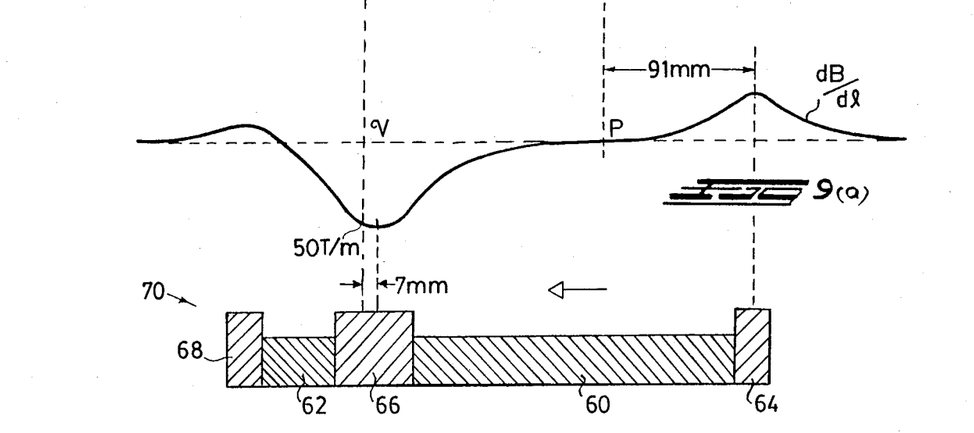
Figure 9B:
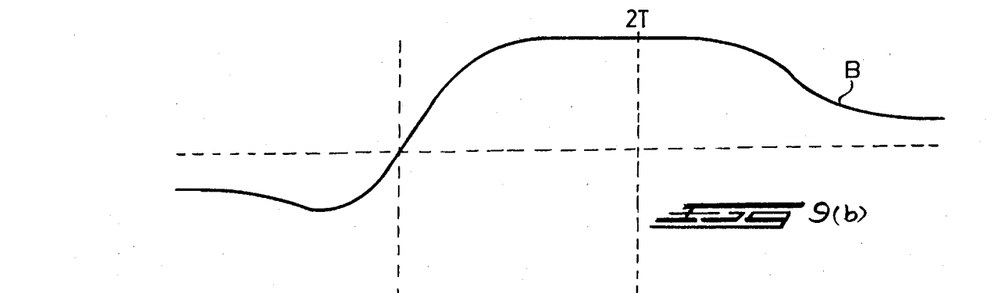

The symmetrical back-to-back arrangement of identical permanent magnet stacks, as shown in FIG. 6, is generally preferred in the construction of a test head according to the invention. An asymmetrical composite head may however be acceptable for certain applications. FIGS. 9(a) and 9(b) are similar to FIGS. 7(a) and 7(b) respectively and, superimposed on these Figures, is a representation of one half of an asymmetrical test head 70 which is similar to that of FIG. 6 except that the leading permanent magnet stacks 60 each include 15 magnets while the lagging permanent magnet stacks 62 each include 3 magnets. Thus the head has the same length and mass as the symmetrical head of FIG. 6. In these Figures rope movement takes place from right to left. The curves of FIGS. 9(a) and 9(b) were obtained for a rope speed of 0.6 meter/second.

The measurements to detect the area variations and broken wires are taken at point p which is 91 mm from the centre of the leading south pole 64 and at which the flux density is 2 Tesla and is substantially constant.

Contact irregularities are measured at point q which is offset approximately 7 mm from the centre of the north pole 66 towards the lagging south pole 68. At this point the flux is zero and $dB/dl = 50$ Tesla per meter.

Clearly other variations in the arrangement of the test head are possible with a greater or lesser number of magnets being used on either side of the central north pole 66.

For composite test heads of the kind described the stronger array of permanent magnets brings the rope to a repeatable saturation flux density condition before demagnetisation of the rope occurs due to the effect of the lagging magnetic field. The stronger head should thus be encountered first. As indicated the relevant portion of the hysteresis curve (FIG. 8) from point c, i.e. at a saturation flux density level through to d, at which stage the flux density equals zero, and then to some point between d and e, is repeatable.

Because of the offset of the point at which the flux density in the rope equals zero unidirectional rope testing is preferred. However with a symmetrical head with a sufficiently high magnetising force this offset is acceptably small and bi-directional tests are possible. In an asymmetrical arrangement where the lagging field is small in order to minimise costs it is possible that unidirectional tests only will be acceptable.

It is to be understood that the test head shown in FIG. 6 can be implemented in a variety of forms. As has already been stated the various transducers, search coils, instrumentation and the like needed for recording the various signals have not been described in detail for they are known in the art. The present invention is particularly directed to the incorporation of the basic theoretical principles hereinbefore outlined in a single instrument which is capable of providing separate measurements for each of the three rope characteristics of interest and the type of measuring devices employed plays no inventive role in the provision of the instrument. By way of example however such instrumentation may include search coils or Hall-effect devices for making the various flux measurements, and other known transducers or apparatus for measuring the rope speed or the rope length during a test, for providing signals for driving a recorder synchronously with rope travel or rope length, for providing signals for compensating rope speed variations in the signal processing system, for providing signals to ensure that the data is processed synchronously with rope speed or rope length, and the like.

It is apparent that higher accuracies are achieved with the test head of the invention as the magnetic fields are increased. Anisotropic strontium ferrite permanent magnets were employed in the test heads of FIGS. 6 and 9 but stronger magnets such as cobalt-samarium permanent magnets, or neodymium-iron-boron permanent magnets, make it possible either to achieve higher magnetic fields which could lead to higher testing speeds, or to achieve the same fields with a smaller structure.

I claim:

1. A method of simultaneously testing a wire rope for multiple types of defect which includes the steps of causing the rope to move axially in a first direction along a generally linear path, establishing a first steady state magnetic field along a first portion of the path whereby a magnetic flux in a first axial direction is produced in the rope, the first magnetic field having a first polarity and being of a strength sufficient to cause a portion of the rope disposed along said first path portion to be magnetically saturated, establishing a second steady state magnetic along a second adjacent portion of the path, the second magnetic field having a second polarity which is opposite to said first polarity and a strength sufficient to produce magnetic saturation in the rope whereby a magnetic flux in a second axial direction opposite to said first axial direction is produced in the rope, the second axial direction opposing the first axial direction and the location of establishment of said fields being selected such that said fields intersect at the region of the junction of said first and second path portions whereby the magnetic flux density in the rope resulting from the influence of said fields has a zero value in the vicinity of the said junction of said first and second path portions, monitoring the magnetic field about the rope in the vicinity of said junction to detect flux variations which result from eddy currents induced in the rope, the flux variations being commensurate with irregularities in the contact pattern of the wires comprising the rope, and monitoring variations in the magnetic flux in the rope at a position along at least one of the said first path portion or the said second path portion where the magnetic flux density gradient in the rope relative to the length of the rope is substantially zero to thereby detect magnetic flux variations which are caused by broken wires in the rope.

2. A method according to claim 1 which further includes the step of monitoring variations in the magnetic flux in the rope at a position within the other of said first path portion or the said second path portion where the magnetic flux density gradient relative to the length of the rope is substantially zero to thereby detect magnetic flux variations which are caused by changes in the cross-sectional area of the rope.

3. Apparatus for testing a rope for defects, said apparatus including means defining a pathway along which the rope is caused to travel in an axial direction, first permanent magnet means for establishing a first steady state magnetic field which extends over at least a first portion of the pathway in a first axial direction, second permanent magnet means for establishing a second steady state magnetic field which extends over at least a second portion of the pathway in a second axial direction, the second axial direction opposing said first axial direction, said first and second magnetic fields being of sufficient strength to cause the rope to become substantially magnetically saturated, a common pole piece disposed between said first and second magnet means whereby the net magnetic flux density at a location in the vicinity of said common pole piece will be zero, first sensor means positioned at said location for detecting variations in the flux produced by eddy currents induced in the rope as a result of irregularities in the contact pattern of the wires in the rope, and second sensor means positioned along one of said first portion or said second portion the pathway at a point where the magnetic flux density gradient in the rope relative to the length of the rope is substantially zero for detecting variations in the magnetic flux established in the rope caused by broken wires in the rope.

4. Apparatus according to claim 3 further including third sensor means positioned within the other of said first portion or said second portion of the pathway at a point where the magnetic flux density gradient in the rope relative to the length of the rope is substantially zero for detecting variations in the magnetic flux established in the rope caused by changes in the cross-sectional area of the rope.

5. Apparatus according to claim 3 wherein the first and second magnetic fields are of equal strength and have the same length in the direction of rope travel.

* * * * *